US012797124B2

(12) United States Patent
Govari et al.

(10) Patent No.: US 12,797,124 B2
(45) **Date of Patent: *Nov. 17, 2026**

(54) MULTI-PURPOSE SENSING AND RADIOFREQUENCY (RF) ABLATION SPIRAL ELECTRODE FOR CATHETER

(71) Applicant: Biosense Webster (Israel) Ltd., Yokneam (IL)

(72) Inventors: Assaf Govari, Haifa (IL); Yehuda Algawi, Binyamina (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 608 days.

This patent is subject to a terminal disclaimer.

(21) Appl. No.: 18/352,877

(22) Filed: Jul. 14, 2023

(65) Prior Publication Data

US 2023/0355305 A1 Nov. 9, 2023

Related U.S. Application Data

(63) Continuation of application No. 16/730,128, filed on Dec. 30, 2019, now Pat. No. 11,712,295.

(51) Int. Cl.
*A61B 18/14* (2006.01)
*A61B 5/06* (2006.01)
(Continued)

(52) U.S. Cl.
CPC .......... *A61B 18/1492* (2013.01); *A61B 5/061* (2013.01); *A61B 5/01* (2013.01);
(Continued)

(58) Field of Classification Search
CPC ................ A61B 18/1492; A61B 5/061; A61B 2034/2051; A61B 2018/00791;
(Continued)

(56) References Cited

U.S. PATENT DOCUMENTS 4,938,761 A * 7/1990 Ensslin .............. A61B 18/1442 606/51
5,391,199 A 2/1995 Ben-Haim
(Continued)

FOREIGN PATENT DOCUMENTS

CN 216365245 U 4/2022
EP 3340750 A1 6/2018
(Continued)

OTHER PUBLICATIONS

Extended European Search Reported dated Jun. 1, 2021, from corresponding European Appl. No. 20217531.1.
(Continued)

*Primary Examiner* — Jaymi E Della

(57) ABSTRACT

An electrical apparatus includes a spiral electrode and an interface circuit. The spiral electrode is disposed on a distal end of a probe for insertion into a body of a patient. The interface circuit is configured to (a) transfer a radiofrequency (RF) ablation signal to the electrode for ablating tissue in the body, (b) output a voltage that develops across the electrode in response to an external magnetic field, for measuring a position of the distal end in the body, and (c) transfer electrical current through the electrode for measuring a resistivity that is indicative of tissue temperature in a vicinity of the electrode.

18 Claims, 3 Drawing Sheets

(51) Int. Cl.

| | |
|---|---|
| *A61B 5/01* | (2006.01) |
| *A61B 18/00* | (2006.01) |
| *A61B 34/20* | (2016.01) |

(52) U.S. Cl.

CPC ..... *A61B 5/065* (2013.01); *A61B 2018/00577* (2013.01); *A61B 2018/00791* (2013.01); *A61B 2018/00875* (2013.01); *A61B 2018/1435* (2013.01); *A61B 2018/147* (2013.01); *A61B 2034/2051* (2016.02); *A61B 2034/2053* (2016.02); *A61B 2562/0223* (2013.01); *A61B 2562/0271* (2013.01)

(58) Field of Classification Search

CPC .. A61B 2018/00875; A61B 2018/1435; A61B 2562/0223; A61B 2562/0271; A61B 5/01; A61B 5/065; A61B 2034/2053

See application file for complete search history.

(56) References Cited

U.S. PATENT DOCUMENTS

| | | | |
|---|---|---|---|
| 5,913,854 | A | 6/1999 | Maguire et al. |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2011/0213355 | A1 | 9/2011 | Behnke, II |
| 2012/0029343 | A1 | 2/2012 | Wasson et al. |
| 2012/0303012 | A1 | 11/2012 | Leyh |
| 2013/0281851 | A1* | 10/2013 | Carr ......................... A61B 5/01 607/96 |
| 2014/0266207 | A1 | 9/2014 | Karmarkar et al. |
| 2017/0042614 | A1* | 2/2017 | Salahieh ............ A61B 1/00082 |
| 2017/0354364 | A1* | 12/2017 | Bar-Tal ................ A61B 5/0036 |
| 2017/0354462 | A1 | 12/2017 | Dong et al. |
| 2018/0180684 | A1* | 6/2018 | Govari ................... H05K 1/165 |
| 2018/0214204 | A1* | 8/2018 | Karmarkar ......... A61B 18/1492 |
| 2018/0280658 | A1 | 10/2018 | Govari et al. |
| 2019/0307501 | A1 | 10/2019 | Sartor et al. |

FOREIGN PATENT DOCUMENTS

| | | | |
|---|---|---|---|
| JP | 2018126564 | A | 8/2018 |
| WO | 96/05768 | A1 | 2/1996 |

OTHER PUBLICATIONS

First Search dated May 30, 2025, from corresponding Chinese Application No. 202011620549.2.

First Office Action with English translation dated May 30, 2025, from corresponding Chinese Application No. 202011620549.2.

First Office Action with English translation dated Jul. 17, 2025, from corresponding Chinese Application No. 202011620549.2.

Supplementary Search dated Jul. 17, 2025, from corresponding Chinese Application No. 202011620549.2.

Supplementary Search dated Oct. 29, 2025, from corresponding Chinese Application No. 202011620549.2.

Third Office Action with English translation dated Oct. 29, 2025, from corresponding Chinese Application No. 202011620549.2.

Supplementary Search dated Feb. 11, 2026, from corresponding Chinese Application No. 202011620549.2.

Search Report dated Jun. 19, 2024, from corresponding Japanese Application No. 2020-218528.

Decision to Grant a Patent dated Jul. 9, 2024, from corresponding Japanese Application No. 2020-218528.

* cited by examiner

MULTI-PURPOSE SENSING AND RADIOFREQUENCY (RF) ABLATION SPIRAL ELECTRODE FOR CATHETER

CROSS-REFERENCE TO RELATED APPLICATIONS

This application is a Continuation application of U.S. patent application Ser. No. 16/730,128 filed Dec. 30, 2019, now U.S. Pat. No. 11,712,295, the entire contents of which is incorporated herein by reference as if fully set forth below.

FIELD OF THE INVENTION

The present invention relates generally to medical probes, and particularly to cardiac sensing and ablation catheters.

BACKGROUND OF THE INVENTION

Cardiac catheters for tissue ablation may include multiple sensors and ablation electrodes at their distal end with the different devices typically electrically isolated one of the other. For example, temperature sensors may be embedded in an area covered by an ablation electrode to measure an ablation temperature of that electrode, but have separate electrical conductors.

SUMMARY OF THE INVENTION

An embodiment of the present invention provides an electrical apparatus including a spiral electrode and an interface circuit. The spiral electrode is disposed on a distal end of a probe for insertion into a body of a patient. The interface circuit is configured to (a) transfer a radiofrequency (RF) ablation signal to the electrode for ablating tissue in the body, (b) output a voltage that develops across the electrode in response to an external magnetic field, for measuring a position of the distal end in the body, and (c) transfer electrical current through the electrode for measuring a resistivity that is indicative of tissue temperature in a vicinity of the electrode.

In some embodiments, the spiral electrode is configured as a single axis coil position sensor.

In some embodiments, the spiral electrode is disposed on a first facet of a Printed Circuit Board (PCB), wherein a first end of the spiral electrode is disposed on the first facet and a second end of the spiral electrode is connected to a second facet of the PCB through a via hole.

In an embodiment, the interface circuit includes high-pass filters on the conductors between a source of the RF ablation signal and the electrode.

In another embodiment, the electrical apparatus further includes a surface electrode configured to close an electrical circuit for the RF ablation signal applied by the spiral electrode.

In some embodiments, the interface circuit includes isolation capacitors on electrical conductors between the spiral electrode and a source of the RF ablation signal.

There is additionally provided, in accordance with another embodiment of the present invention, a method including inserting a spiral electrode disposed on a distal end of a probe into a body of a patient. A radiofrequency (RF) ablation signal is transferred to the electrode for ablating tissue in the body. A voltage that develops across the electrode in response to an external magnetic field is outputted for measuring a position of the distal end in the body. Electrical current is transferred through the electrode for measuring a resistivity that is indicative of tissue temperature in a vicinity of the electrode.

There is further provided, in accordance with another embodiment of the present invention, a manufacturing method including disposing a spiral electrode on a distal end of a probe for insertion into a body of a patient. An interface circuit is connected to the spiral electrode, with the interface circuit configured to (a) transfer a radiofrequency (RF) ablation signal to the electrode for ablating tissue in the body, (b) output a voltage that develops across the electrode in response to an external magnetic field, for measuring a position of the distal end in the body, and (c) transfer electrical current through the electrode for measuring a resistivity that is indicative of tissue temperature in a vicinity of the electrode.

In some embodiments, disposing the spiral electrode includes disposing the spiral electrode, including a first end of the electrode, on a first facet of a Printed Circuit Board (PCB), and connecting a second end of the spiral electrode to a second facet of the PCB through a via hole.

The present invention will be more fully understood from the following detailed description of the embodiments thereof, taken together with the drawings in which:

BRIEF DESCRIPTION OF THE DRAWINGS

FIG. 2A is a schematic, pictorial illustration of the catheter tip of the catheter of FIG. 1 comprising a spiral multi-purpose electrode and its conductors while FIG. 2B is another example of a spiral multi-purpose electrode, in accordance with embodiments of the invention.

DETAILED DESCRIPTION OF EMBODIMENTS

Overview

Figure 1:
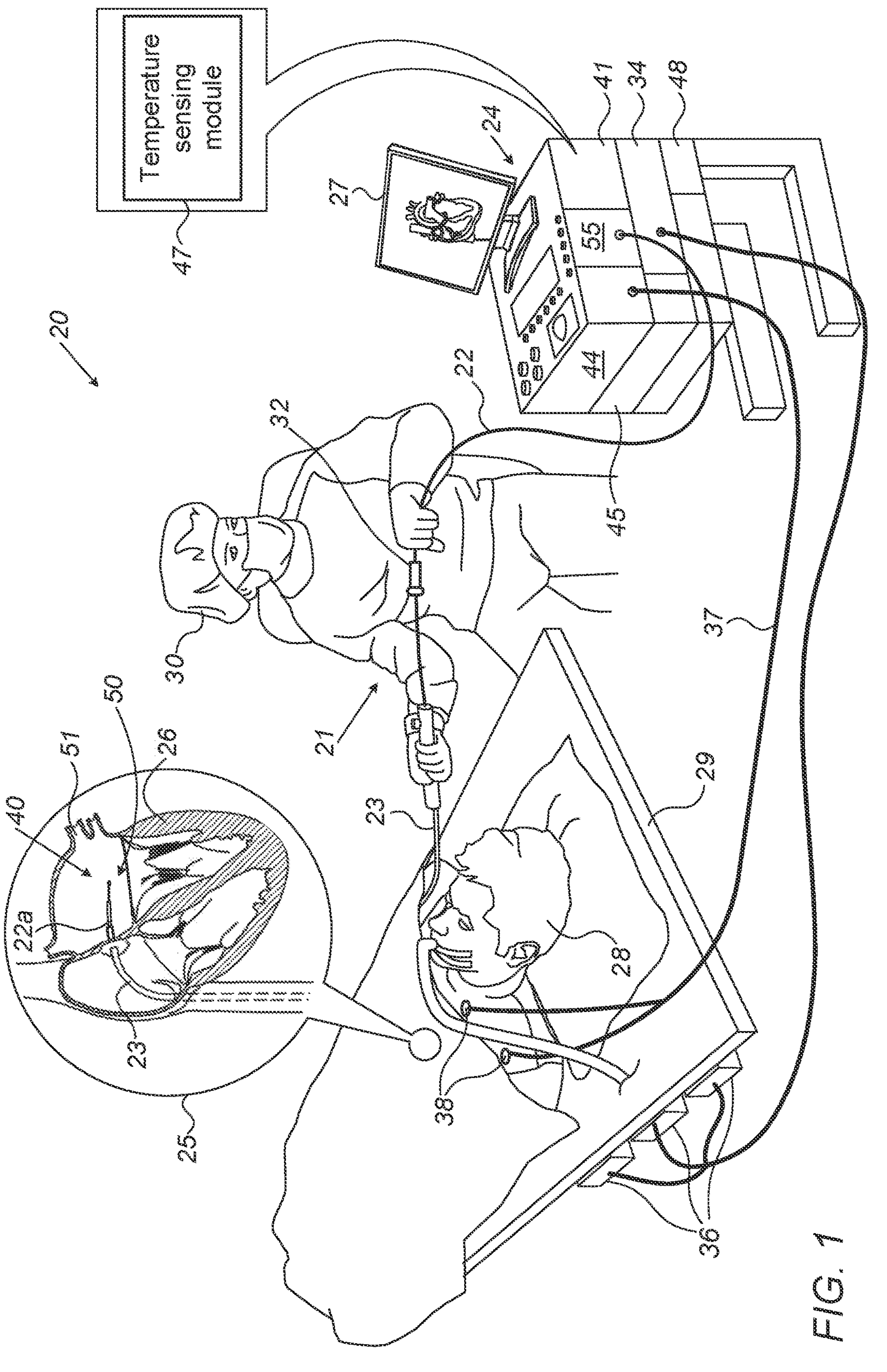
FIG. 1 is a schematic, pictorial illustration of a catheter-based position-tracking and radiofrequency (RF) ablation system, in accordance with an embodiment of the present invention.

A catheter used for radiofrequency (RF) ablation requires an electrode capable of delivering the ablation power. In addition, the catheter position may be tracked, and electrode temperature measured during ablation. These three conditions may be served by three separate systems: an electrode, a tracking device such as a single- or triple-axis magnetic sensor, and a temperature sensor such as a thermocouple. The three separate systems require three separate sets of connections, some of which may themselves be problematic. (For example, the constantan in copper-constantan thermocouples is brittle and easily broken.) Notwithstanding the existence of problems, integration of three separate systems on a tip of a catheter tip is inherently complicated.

Embodiments of the present invention that are described hereinafter use one electrode which is able to provide the three functions. In some embodiments, a spiral electrode is disposed on a distal end of a probe for insertion into a body of a patient. An interface circuit of an electrical apparatus is configured to (a) transfer a radiofrequency (RF) ablation signal to the electrode for ablating tissue in the body, (b) output a voltage that develops across the electrode in response to an external magnetic field, for measuring a position of the distal end in the body, (c) and transfer electrical current through the electrode for measuring a resistivity that is indicative of tissue temperature in a vicinity of the electrode.

In some embodiments, the electrode is formed as a planar high-density spiral on one side of a flexible printed circuit board (PCB), with one end of the spiral being connected on one facet of the PCB. The other facet of the PCB is used to connect to the other end of the spiral through a plated hold ("via") in the PCB. The spiral is typically formed from metal, such as gold. In one embodiment, the spiral is in the form of an approximately 4 mm×4 mm square, the lines of the spiral being approximately 25 μm wide separated by approximately 25 μm. Any general spiral shape in rectilinear, curves or curvilinear spiral is possible, and in particular elliptical or circular shapes may be utilized.

As used herein, the terms "about" or "approximately" for any numerical values or ranges indicate a suitable dimensional tolerance that allows the component or collection of components to function for its intended purpose as described herein. More specifically, "about" or "approximately" may refer to the range of values ±20% of the recited value, e.g. "about 90%" may refer to the range of values from 71% to 99%.

The spiral has a large area, and thus is able to transfer RF ablation power and act as an ablation electrode. Furthermore, since the ablation RF power is connected to both ends of the spiral, as shown below, no RF power is transferred along the lines of the spiral. Instead, all the power transfers out from the spiral surface, through the patient, and to a return electrode attached to the patient's skin. The ablation RF power typically has a frequency range of 350-500 kHz, which, in an embodiment, is provided to the spiral electrode through isolating capacitors (or other suitable high-pass filters), as shown below.

Since the electrode is in the form of a spiral, it can act as a single axis magnetic sensor that is responsive to alternating magnetic fields traversing the spiral electrode, the fields generating potentials $V_f$ across the two ends of the spiral. (The alternating magnetic fields have frequencies typically equal to approximately 20 kHz, so they can be easily isolated from the ablation power, using, for example, isolating capacitors). The potentials $V_f$ can be used to find the position and orientation of the sensor, so that the electrode acts as a location sensor.

The specific resistance of the metal (e.g., gold) spiral changes with its with temperature, in a very well-known relation (the temperature coefficient of gold is 0.003715° $C.^{-1}$). Measuring the resistance R of the spiral thus provides a measure of the temperature. For example, a gold spiral having a resistance of 30Ω (the approximate resistance of the 4 mm×4 mm spiral described above) at 20° C. has a resistance of 30.1Ω at 21° C. The resistance R of the spiral may be measured using an impedance reading circuitry, for example, by connecting the spiral as one arm of a Wheatstone bridge. The electrode can thus act as a resistance thermometer. In an embodiment, the aforementioned electrically isolating capacitors ensure that the resistance measured is that of the spiral.

There is no restriction as to the type of catheter for which a spiral of the invention may be used, i.e., the spiral may be incorporated into a focal, basket, balloon, lasso, or other type of catheter.

There is also no requirement for implementation of all three functions of a spiral. Thus, in some embodiments only one function is used, in other embodiments only two of the three functions are used, and in other embodiments all three functions are used.

By providing a multipurpose electrode of a catheter as described above, the complexity and price of a catheter may be lowered and thereby increase availability of catheter-based RF ablation treatments.

System Description

FIG. 1 is a schematic, pictorial illustration of a catheter-based position-tracking and radiofrequency (RF) ablation system 20, in accordance with an embodiment of the present invention. System 20 comprises a catheter tip 40 (seen in inset 25) that is fitted at a distal end 22*a* of a shaft 22 of a catheter 21. RF ablation tip 40 comprises a spiral electrode 50 (detailed in FIG. 2A) that further acts as a magnetic sensor and as a temperature sensor. In the embodiment described herein, spiral electrode 50 is used to ablate tissue of an ostium 51 of a PV in a heart 26.

The proximal end of catheter 21 is connected to a control console 24 comprising an RF ablative power source 45. An ablation protocol comprising ablation parameters is stored in a memory 48 of console 24.

Physician 30 inserts distal end 22*a* of shaft 22 through a sheath 23 into heart 26 of a patient 28 lying on a table 29. Physician 30 advances the distal end of shaft 22 to a target location in heart 26 by manipulating shaft 22 using a manipulator 32 near the proximal end of the catheter and/or deflection from the sheath 23. During the insertion of distal end 22*a*, catheter tip 40 is maintained inside sheath 23 to minimize vascular trauma along the way to target location.

In an embodiment, physician 30 navigates the distal end of shaft 22 to the target location by tracking a direction of catheter tip 40. During navigation of distal end 22*a* in heart 26, console 24 receives signals from spiral electrode 50 at catheter tip 40, which acts as a magnetic sensor in response to magnetic fields from external field generators 36. Magnetic field generators 36 are placed at known positions external to patient 28, e.g., below patient table 29. Console 24 also comprises a driver circuit 34, configured to drive magnetic field generators 36.

For example, using the signal, a processor 41 of the system estimates a direction of catheter tip 40 in the heart and, optionally, presents the tracked direction on a display 27, e.g., relative to an orientation of an axis of approximate symmetry of ostium 51. In an embodiment, console 24 drives a display 27, which shows the tracked position of catheter tip 40 inside heart 26.

The method of direction sensing using external magnetic fields is implemented in various medical applications, for example, in the CARTO™ system, produced by Biosense-Webster and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, which prior applications are hereby incorporated by reference in their entirety herein into this application as if set forth in full with a copy attached in the Appendix. In an embodiment, signals from spiral electrode 50 are further used for position sensing using the aforementioned CARTO™ system.

Once distal end 22*a* of shaft 22 has reached heart 26, physician 30 retracts sheath 23 and further manipulates shaft 22 to navigate catheter tip 40 to an ostium 51 the pulmonary vein. Next, while catheter tip 40 contacts the tissue, the physician causes RF electric currents to be passed between spiral electrode 50 on tip 40 and an indifferent (i.e., neutral) electrode patch that is coupled externally to the subject, e.g., to the subject's back. The patch can be a single electrode or made of several electrodes, such as electrodes 38, which are shown connected by wires running in a cable 37. Processor 41 adjusts the parameters of the ablating currents by outputting appropriate instructions to RF generator 45 that generates the currents.

To further perform its functions, processor 41 includes a temperature sensing module 47. In the exemplified system, temperature sensing module 47 receives electrical impedance signals, measured between the two ends of spiral electrodes 50 and conducted by wires running through shaft 22 to processor 41.

Processor 41 is typically a general-purpose computer, with suitable front end and (a) ECG interface circuits 44 for receiving ECG signals from electrodes 38, and (b) an electrical interface circuit 55 for receiving signals from catheter 21, as well as for applying RF energy treatment via catheter 21 in a left atrium of heart 26 and for controlling the other components of system 20. Processor 41 typically comprises a software in a memory 48 of system 20 that is programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIG. 3, that enables processor 41 to perform the disclosed steps, as further described below.

While FIG. 1 describes a tip catheter, the principles of the present technique apply to any catheter having a distal end fitted with multiple electrodes, such as Pentaray and Octaray catheters (made by Biosense-Webster).

Multi-Purpose Sensing and RF Ablation Spiral Electrode for Catheter

Figures 2A, 2B:
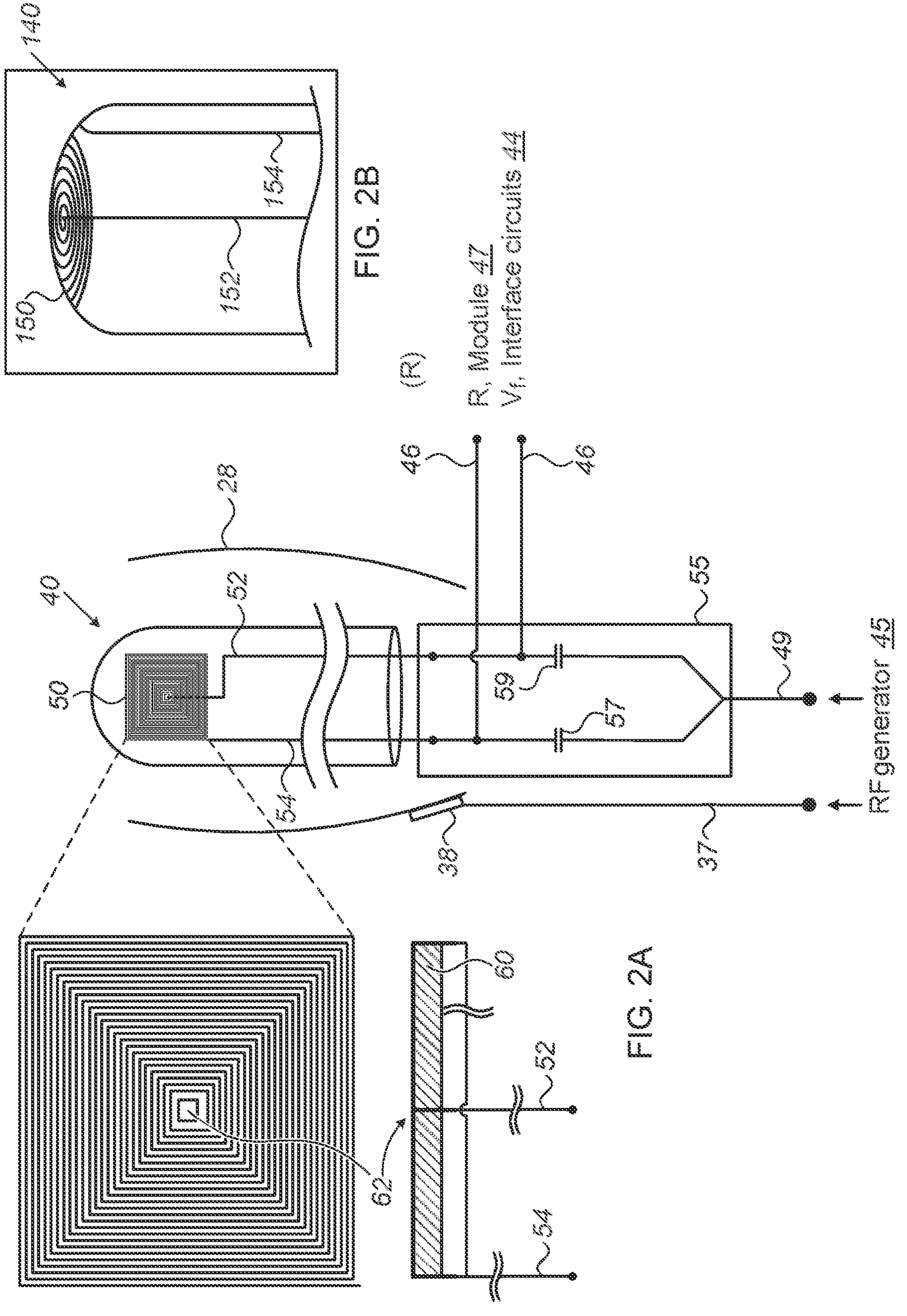

FIG. 2A is a schematic, pictorial illustration of catheter tip 40 of the catheter of FIG. 1 comprising a spiral multi-purpose electrode 50 and its electrical interface circuit 55, in accordance with an embodiment of the invention. Electrical interface circuit 55 comprises conductors (52, 54, 46, 49) and capacitors (57, 59) or other suitable high-pass filters, and is used for (a) transferring a radiofrequency (RF) ablation signal to electrode 50 for ablating tissue in the body, (b) outputting a voltage that develops across electrode 50 in response to an external magnetic field, for measuring a position of the distal end in the body, and (c) transferring electrical current through electrode 50 for measuring a resistivity that is indicative of tissue temperature in a vicinity of electrode 50.

As seen, electrode 50 is formed as a 2D planar high-density metal spiral. While the shown outline of the spiral electrode is of a square, any general rectilinear, curve or curvilinear spiral shape is possible, and in particular elliptical or circular shapes. In an embodiment, the metal spiral is disposed on a flexible PCB 60, seen in cross-section. However, other types of substrates that can be manufactured to conform to the shape of the tip may be used. As further seen, the center of the spiral is electrically connected to a conductor 52 on the backside of the PCB, using a via 62 in PCB 60. The perimeter of the spiral is connected to a conductor 54.

Spiral electrode 50 is able to transfer RF ablation power and act as an ablation electrode. Furthermore, since the ablation RF power is connected to both ends of the spiral, i.e., by short circuiting conductors 52 and 54 into a single conductor 49 (proximally to isolating capacitors 57 and 59), no RF power is transferred along the lines of the spiral, with all the power transferred by conductor 49, out from the spiral surface, through the patient, to a return electrode 38 attached to the patient skin, and further via cable 37 to close an electrical circuit at generator 45 output leads.

Further shown are conductors 46. Spiral electrode 50 can act as a single axis magnetic sensor that is responsive to alternating magnetic fields traversing the spiral electrode, the fields generating potentials $V_f$ across the two ends of conductors 46. (The alternating magnetic fields have frequencies typically equal to approximately 20 kHz, so they can be easily isolated from the ablation power using capacitors 57 and 59.) The low frequency potentials $V_f$ can be used to find the position and orientation of the sensor, so that the electrode acts as a location sensor.

The metal of the spiral changes its specific resistance with temperature, in a very well-known relation, which depends on the composition of the electrode material. Measuring the resistance R of the spiral between conductors 46 thus provides a temperature measurement using module 47. The spiral electrode can thus act as a resistance thermometer. In an embodiment, the aforementioned electrically isolating capacitors 57 and 59 ensure that the resistance measured is that of the spiral itself, and not, for example, a resistance weighted by the output resistance of generator 45.

As shown in FIG. 2B, the disclosed spiral electrode 150 can alternatively be disposed on a three-dimensional dome-shaped distal tip 140 of a catheter, whereby a flexible PCB with the spiral traces is conformed over the dome. As further seen, spiral electrode 150 is disposed in this three-dimensional shape, with the center of the spiral being electrically connected to a conductor 152 and the perimeter of the spiral is connected to a conductor 154.

The pictorial side view shown in FIGS. 2A and 2B is chosen by way of example, where other embodiments are possible. For example, in another embodiment, cooling fluid flows via irrigation holes (not shown) in electrodes 50 to cool ablated tissue.

Figure 3:
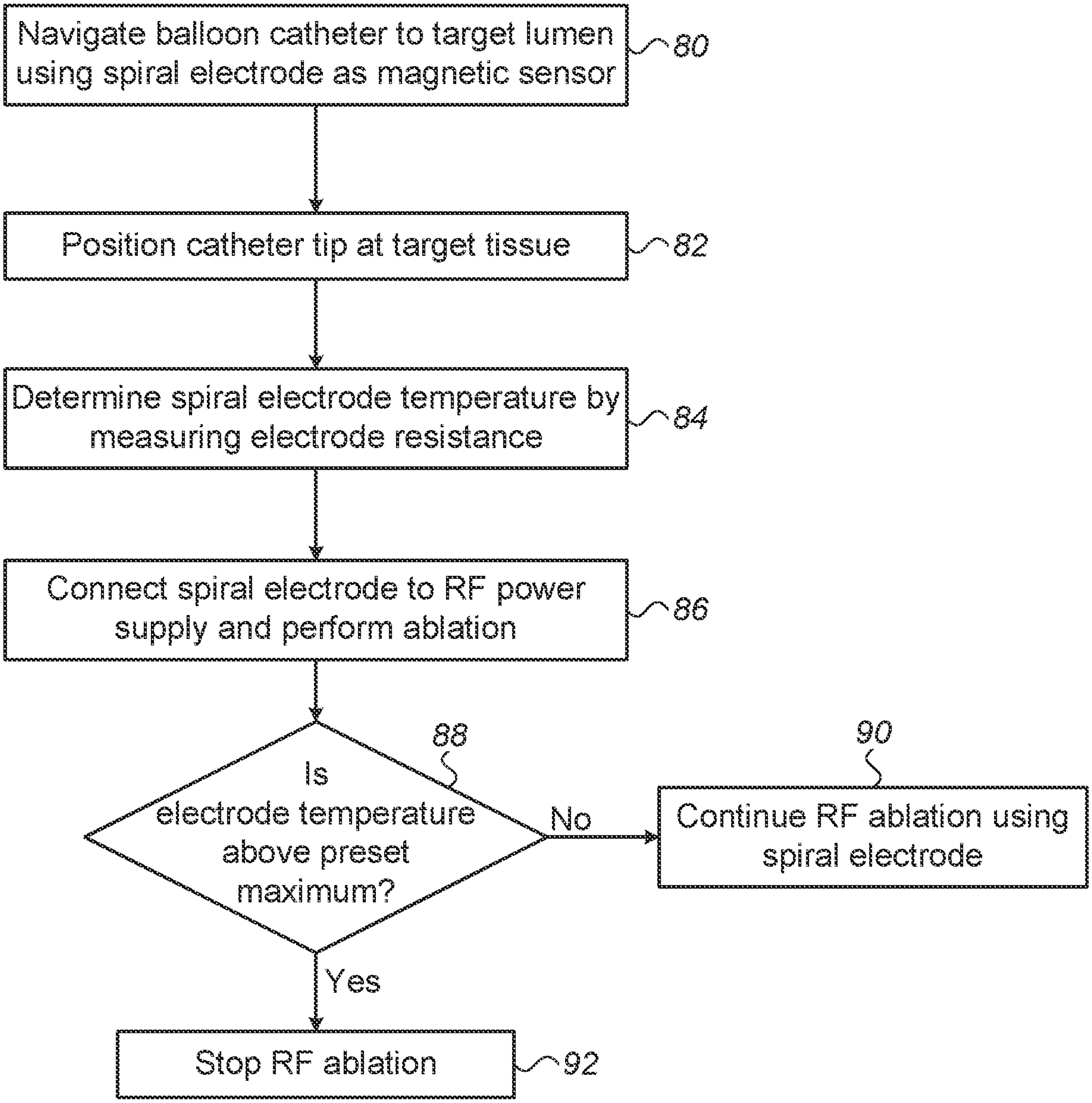
FIG. 3 is a flow chart that schematically illustrates a method for using the spiral electrode of the catheter tip of FIG. 2A or 2B for position sensing, radiofrequency (RF) ablation, and temperature sensing, in accordance with an embodiment of the invention.

FIG. 3 is a flow chart that schematically illustrates a method for using spiral electrode 50 of catheter tip 40 of FIG. 2A or 2B for position sensing, radiofrequency (RF) ablation, and temperature sensing, in accordance with an embodiment of the invention. The algorithm, according to the presented embodiment, carries out a process that begins when physician 30 navigates catheter tip 40 to a target tissue location within heart 26 of a patient, such as at ostium 51, using spiral electrode 50 as a magnetic sensor, at a catheter tip navigation step 80.

Next, physician 30 positions the catheter tip at ostium 51, at a catheter tip positioning step 82. In the process, physician 30 brings catheter tip 40 into contact with target tissue.

Next, processor 41 measures, using impedance sensing module 47, the resistance of spiral electrode 50, to determine electrode temperature, at an electrode temperature measurement step 84.

Next, physician 30 controls interface circuits 44 to connect spiral electrode 50 to RF power supply 45 and to apply ablative energy via spiral electrode 50, at an RF ablation step 86.

During application of ablative energy, processor 41 measures electrode 50 temperature and compares the measured temperature to a preset maximal temperature, at a temperature checking step 88.

If the temperature is below the preset maximal temperature, processor 41 controls interface circuits 44 to continue applying the RF power via electrode 50, at a continued RF power application step 90.

If, on the other hand, the temperature is above the preset maximal temperature, processor 41 controls interface circuits 44 to disconnect the RF power source from electrode 50, at a switching RF power off step 92.

The example flow chart shown in FIG. 3 is chosen purely for the sake of conceptual clarity. In alternative embodiments, additional steps may be performed, such as comparing the temperature of electrode 50 to a minimal preset temperature and disconnecting electrode 50 from the RF power source if the temperature of electrode 50 has not exceeded the minimal preset temperature within a given time duration after the start of application of ablative RF energy (indicative of electrode immersed in blood).

Although the embodiments described herein mainly address pulmonary vein isolation, the methods and systems described herein can also be used in other applications that require RF ablation of body tissue, such as, for example, in renal denervation, cerebrovascular applications and in otolaryngology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical system, comprising:

a probe configured for insertion into an organ of a body of a patient, the probe comprising a distal tip;

an electrode disposed on the distal tip, the electrode connected to a first conductor and a second conductor, the first conductor and the second conductor both being short circuited to a single conductor proximal to the electrode; and an interface circuit configured to:

transfer a radiofrequency (RF) ablation signal configured to ablate tissue in the body via the single conductor to the first and second conductors and to the electrode; and output a voltage via the first and second conductors that develops across the electrode in response to an external magnetic field configured to measure a position of the distal tip in the body.

2. The medical system of claim 1, the interface circuit further configured to measure a resistivity through the electrode that is indicative of tissue temperature in a vicinity of the electrode via the first and second conductors.

3. The medical system of claim 1, the electrode comprising a spiral electrode.

4. The medical system of claim 3, the spiral electrode being configured as a single axis coil position sensor.

5. The medical system of claim 1, the distal tip comprising a dome-shaped distal tip, wherein the electrode is conformed over the dome-shaped distal tip.

6. The medical system of claim 1, the interface circuit comprising high-pass filters in electrical communication with the first and second conductors and located between the single conductor and the electrode.

7. The medical system of claim 1, the interface circuit comprising isolation capacitors on the first and second conductors between the electrode and the single conductor.

8. The medical system of claim 1 further comprising a surface electrode configured to be disposed on a surface of the body of the patient and configured to close an electrical circuit for the RF ablation signal transferred to the electrode.

9. The medical system of claim 1, wherein the electrode is disposed on a first facet of a printed circuit board (PCB), wherein a first end of the electrode is disposed on the first facet and a second end of the electrode is connected to a second facet of the PCB through a via hole.

10. The medical system of claim 2 further comprising a processor configured to determine whether the tissue temperature is greater than a predetermined temperature.

11. The medical system of claim 10, the processor further configured to, in response to determining that the tissue temperature is less than the predetermined temperature, cause the electrode to transfer the RF ablation signal via the single conductor to the first and second conductors and to the electrode to ablate the tissue in the body.

12. The medical system of claim 11, the processor further configured to, in response to determining that the tissue temperature is greater than the predetermined temperature, stop the RF ablation signal.

13. A method comprising:

inserting a medical probe into a body of a patient, the medical probe comprising an electrode disposed at a distal tip, the electrode in electrical communication with a first conductor and a second conductor, the first conductor and the second conductor both being electrically shorted to a single conductor proximal the electrode;

navigating the medical probe to an organ of the patient using a voltage that develops across the electrode in response to an external magnetic field configured to measure a position of the distal tip in the body;

in response to determining that the distal tip is positioned at tissue in the organ, transferring a radio frequency (RF) ablation signal to the first and second conductors and the electrode via the single conductor, the electrode being configured to ablate the tissue in the body; and measuring a resistivity of the electrode, the resistivity being indicative of tissue temperature in a vicinity of the electrode.

14. The method of claim 13, wherein the voltage that develops across the electrode in response to the external magnetic field is output via the first and second conductors.

15. The method of claim 13, wherein measuring the resistivity of the electrode further comprises transferring an electrical current via the first and second conductors through the electrode.

16. The method of claim 13 further comprising determining whether the tissue temperature is greater than a predetermined temperature.

17. The method of claim 16 further comprising, in response to determining that the tissue temperature is less than the predetermined temperature, causing the electrode to transfer the RF ablation signal to ablate the tissue in the body.

18. The method of claim 17 further comprising, in response to determining that the tissue temperature is greater than the predetermined temperature, stopping the RF ablation signal.

* * * * *